US007180061B2

(12) United States Patent
Lu

(10) Patent No.: US 7,180,061 B2
(45) Date of Patent: Feb. 20, 2007

(54) METHOD FOR ELECTRON BEAM-INITIATED COATING FOR APPLICATION OF TRANSMISSION ELECTRON MICROSCOPY

(75) Inventor: Wei Lu, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 8 days.

(21) Appl. No.: 10/711,644

(22) Filed: Sep. 29, 2004

(65) Prior Publication Data

US 2006/0065829 A1     Mar. 30, 2006

(51) Int. Cl.
G01N 31/00     (2006.01)
G01N 33/00     (2006.01)
G01N 23/00     (2006.01)
G21K 7/00      (2006.01)

(52) U.S. Cl. ...................... 250/307; 250/304
(58) Field of Classification Search ................ 250/307, 250/304
See application file for complete search history.

(56) References Cited

U.S. PATENT DOCUMENTS

| 5,633,502 | A | 5/1997 | Fischione |
| 6,303,399 | B1* | 10/2001 | Engelmann et al. .......... 438/14 |
| 6,576,900 | B2 | 6/2003 | Kelly et al. |
| 6,646,259 | B2* | 11/2003 | Chang et al. ................ 250/307 |
| 6,664,552 | B2 | 12/2003 | Shichi et al. |
| 6,683,304 | B1 | 1/2004 | Jiyan et al. |
| 6,683,305 | B1 | 1/2004 | Lu et al. |
| 6,753,538 | B2* | 6/2004 | Musil et al. ............. 250/492.2 |
| 2002/0166976 | A1 | 11/2002 | Sugaya et al. |

* cited by examiner

Primary Examiner—Jack Berman
Assistant Examiner—Jennifer Yantorno
(74) Attorney, Agent, or Firm—Cantor Colburn LLP

(57) ABSTRACT

A method for preparing a specimen for application of microanalysis thereto includes forming an initial conductive layer over a defined area of interest on a semiconductor substrate, the initial conductive layer formed through an electron beam deposition process. A volume of substrate material surrounding the area of interest is removed, thereby forming the specimen, including said area of interest and said initial conductive layer over the area of interest. The specimen is then removed from the bulk substrate material.

16 Claims, 6 Drawing Sheets

METHOD FOR ELECTRON BEAM-INITIATED COATING FOR APPLICATION OF TRANSMISSION ELECTRON MICROSCOPY

BACKGROUND OF INVENTION

The present invention relates generally to inspection of integrated circuit devices, and, more particularly, to a method for preparing a specimen for application of microanalysis, such as transmission electron microscopy (TEM).

Advancements in Transmission Electron Microscopy, or TEM, technology enables materials to be analyzed at near atomic resolution by providing high-magnification, high-resolution imaging and analysis capabilities. TEM enables scientists to gather information relating to a material's physical properties, such as its microstructure, crystalline orientation and elemental composition. This information has become increasingly important as the need for advanced materials for use in areas such as microelectronics and optoelectronics, biomedical technology, aerospace, transportation systems and alternative energy sources, among others, increases.

TEM is accomplished by examining material specimens under a transmission electron microscope. In a transmission electron microscope, a series of electromagnetic lenses direct and focus an accelerated beam of electrons, emitted from an electron gun contained within the microscope, at the surface of a specimen. Electrons transmitted through the specimen yield an image of the specimen's structure, which provides information regarding its properties. In addition, elemental and chemical information is provided by both the transmitted electrons and the x-rays that are emitted from the specimen's surface as a result of electron interaction with the specimen. Thus, because it is necessary for the electron beam to transmit through the specimen, a key component of successful material analysis by TEM techniques is the condition and preparation of the specimen itself.

Before a specimen can be analyzed using TEM, it must be prepared using various techniques to achieve the necessary electron transparency. This electron transparency is accomplished by thinning a defined area of the specimen. For equal resolution, the required thickness of the specimen is dependent on the accelerating voltage of the transmission electron microscope. For example, using a 120 kV microscope, the specimen thickness must be on the order of about 100 to about 2000 angstroms (Å). In contrast, A 1,000 kV microscope can tolerate a specimen thickness of up to about 5,000 Å.

Specimens are prepared through several well-known methods, including, but not limited to, electrolytic thinning, mechanical grinding, ultramicrotomy, crushing, and ion milling. Often times, multiple methods are utilized to prepare a single specimen. For most types of specimens, either electrolytic thinning or ion milling is used as the final form of specimen preparation. In both cases, amorphous damage ranging in thickness from 1–10 nanometers may result, particularly in the case of ion milling. In this case, the energy of the ion beam transforms the crystalline structure of the material to an amorphous state. This amorphous damage adversely affects the quality of the TEM analysis because it alters the natural characteristics of the material.

Accordingly, one way of protecting a specimen (such as a resist covered substrate) is to deposit a conductive metal layer (e.g., platinum, tungsten, gold, copper, aluminum, titanium, etc.) over the surface by a physical vapor deposition process to release charges from the TEM microscope electron beam bombardment or a focused ion beam etching process. In particular, platinum is a preferred metal because it is a stable metal that can be formed at a very thin thickness. Metal deposition on a selected area is advantageous in that it results in high throughput and lower costs. In addition, the entire wafer is not impacted because of the localized coating, and can be subsequently used in production or development. Moreover, a typically applied process of ion beam initiated metal encapsulation can cause edge roundness, flat top edge rounding and blurred boundary definition, which raises a serious issue if TEM is used to place emphasis on the feature topography, such as true feature boundary definition for critical dimension (CD) measurement. The critical dimension measurement can in turn qualify the TEM as a high-resolution metrology reference system for semiconductor metrology.

SUMMARY OF INVENTION

The foregoing discussed drawbacks and deficiencies of the prior art are overcome or alleviated by a method for preparing a specimen for application of microanalysis thereto. In an exemplary embodiment, the method includes forming an initial conductive layer over an area of interest, the initial conductive layer formed through a low-energy beam deposition process. A volume of material surrounding the area of interest is removed by forming a pair of trenches in a bulk material having the area of interest formed thereon, thereby forming a membrane including the area of interest and the initial conductive layer over the area of interest. The membrane is then removed from the bulk material.

In another embodiment, a method for preparing a specimen for application of microanalysis thereto includes forming an initial conductive layer over a defined area of interest on a semiconductor substrate, the initial conductive layer formed through an electron beam deposition process. A volume of substrate material surrounding the area of interest is removed, thereby forming the specimen, including said area of interest and said initial conductive layer over the area of interest. The specimen is then removed from the bulk substrate material.

BRIEF DESCRIPTION OF DRAWINGS

Referring to the exemplary drawings wherein like elements are numbered alike in the several Figures.

DETAILED DESCRIPTION

Disclosed herein is a method for transmission electron microscopy (TEM) sample preparation in which only the area of interest is covered with a conductive metal layer such as platinum. Briefly stated, an initial thickness of conductive metal (e.g., platinum) is locally formed by electron beam (i.e., low-energy) deposition, which protects the topographic features on the surface of the tested sample. Thereafter, this precoated layer may optionally be coated with additional metal formed by ion beam (i.e., high-energy) deposition for increased throughput. In so doing, the damage created on the surface of interest can be minimized.

Figure 1:
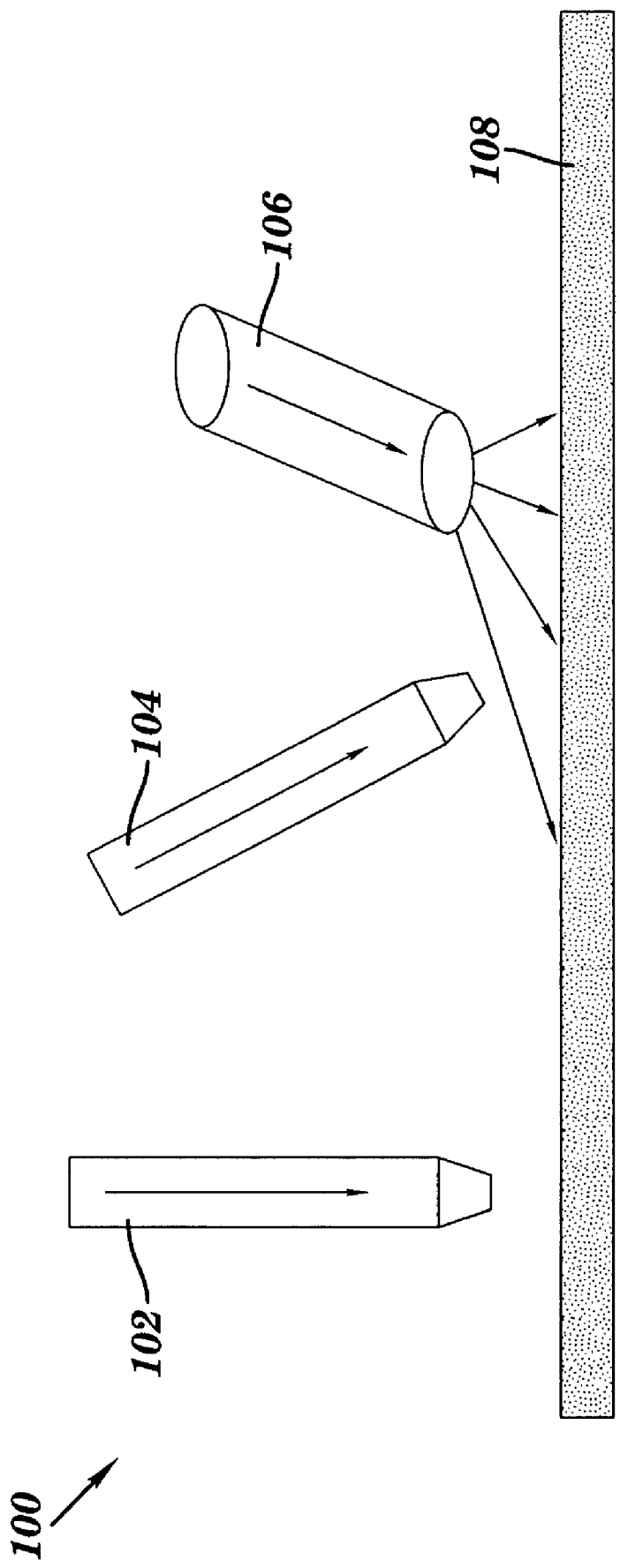
FIG. 1 is a side sectional view of a tunneling electron microscopy (TEM) preparation system suitable for use in accordance with an embodiment of the invention.
Figure 2:
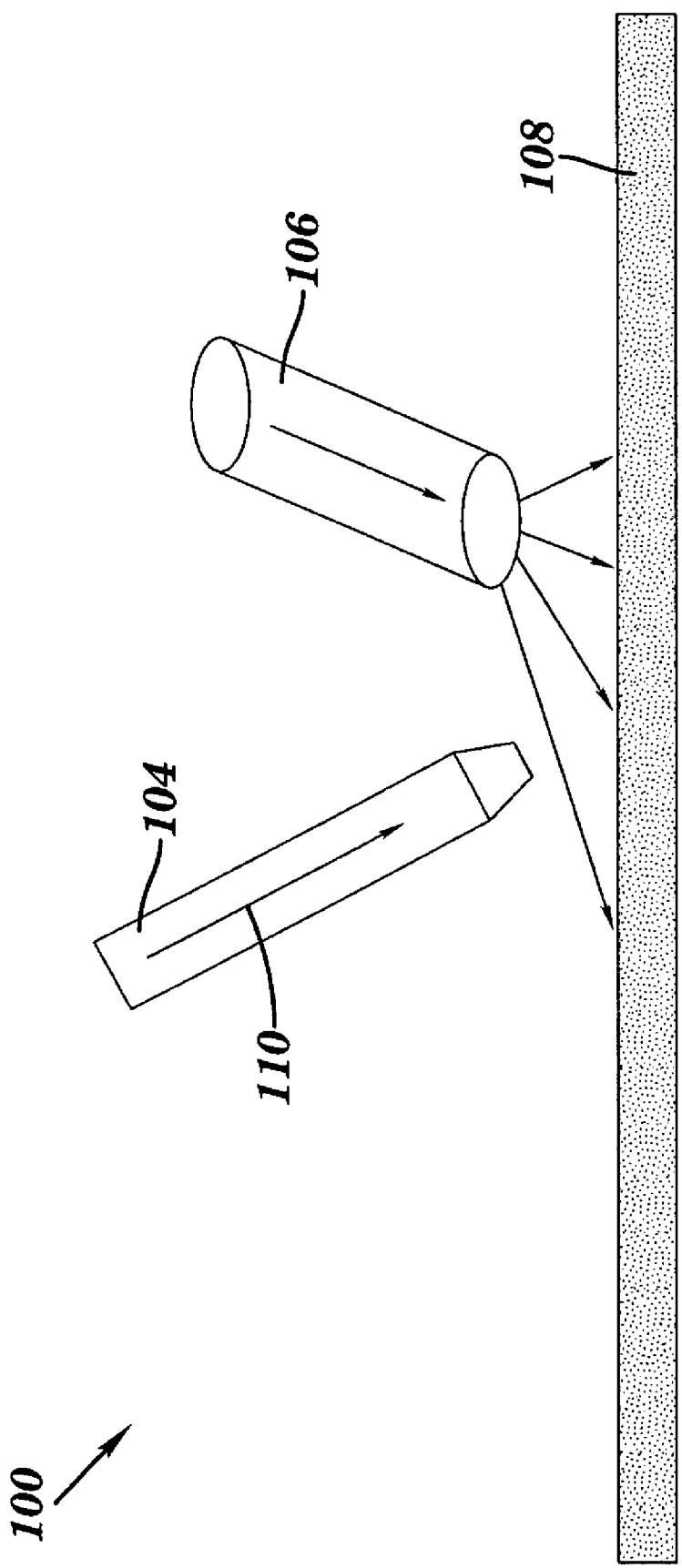
FIG. 2 is another view of the TEM preparation system of FIG. 1, focusing on the SEM column and precursor delivering tube.

Referring initially to FIG. 1, there is shown a side sectional view of a tunneling electron microscopy (TEM) preparation system 100 suitable for use in accordance with an embodiment of the invention. System 100 includes a focused ion beam (FIB) column 102, a scanning electron microscope (SEM) column 104 and a precursor delivering tube 106 for supplying a precursor gas (e.g., methylcyclopentadienyl platinum ($CH_3C_5H_4$)($CH_3$)3Pt)) to assist with metal deposition upon the surface of a semiconductor wafer 108. FIG. 2 is another view of the TEM preparation system, focusing on the SEM column 104 and precursor delivering tube 106. The SEM column 104 provides a source for a low-energy electron beam 110 that may be manipulated directionally so as to cover an area (topology) of interest on the surface of wafer 108. Depending upon the material softness, the low-energy electron beam may be applied at an energy of about 3 keV or less.

Figure 3:
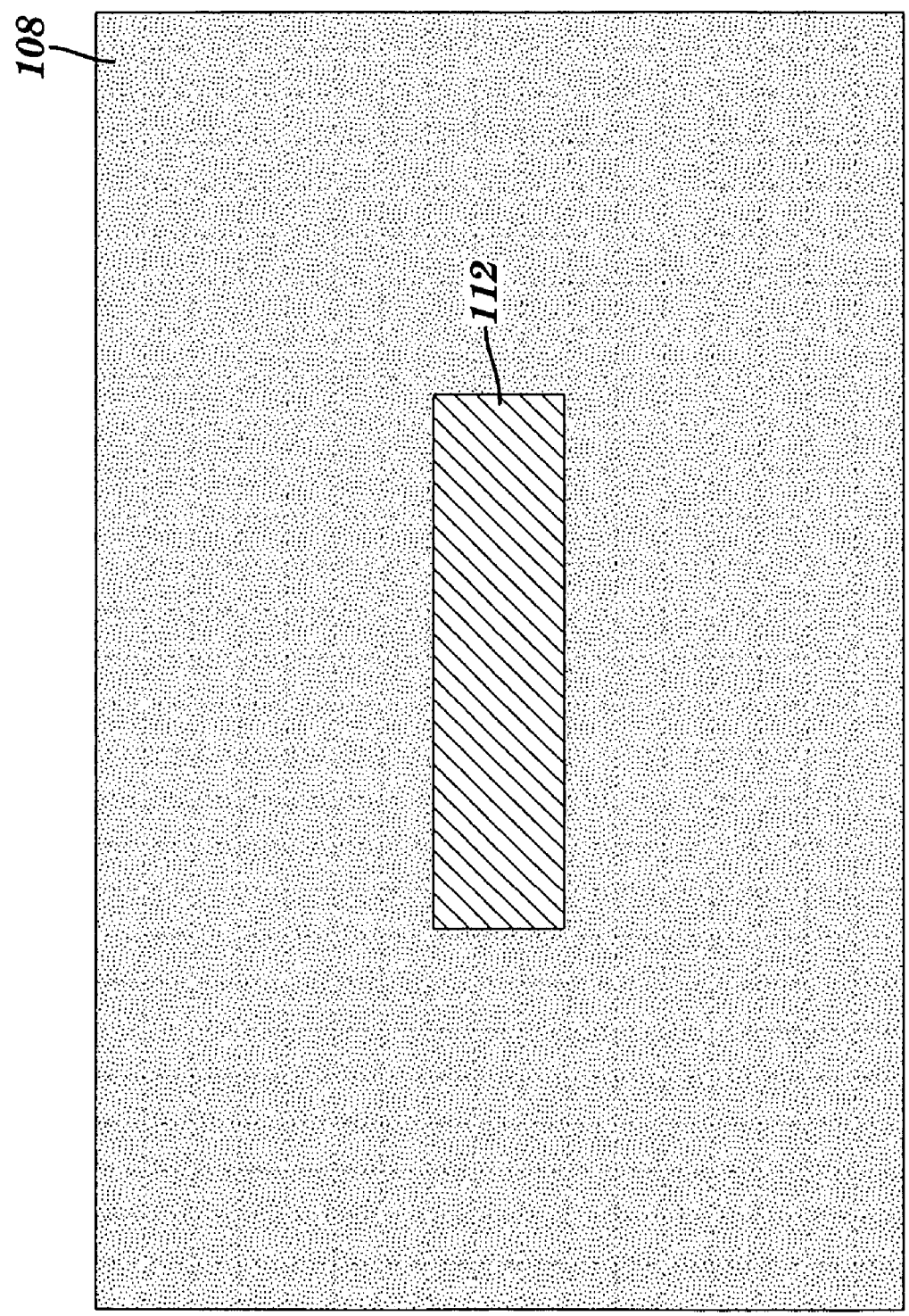
FIG. 3 is a plan view of a localized conductive layer formed on the surface of a semiconductor wafer by electron beam deposition, in accordance with an embodiment of the invention.
Figure 4:
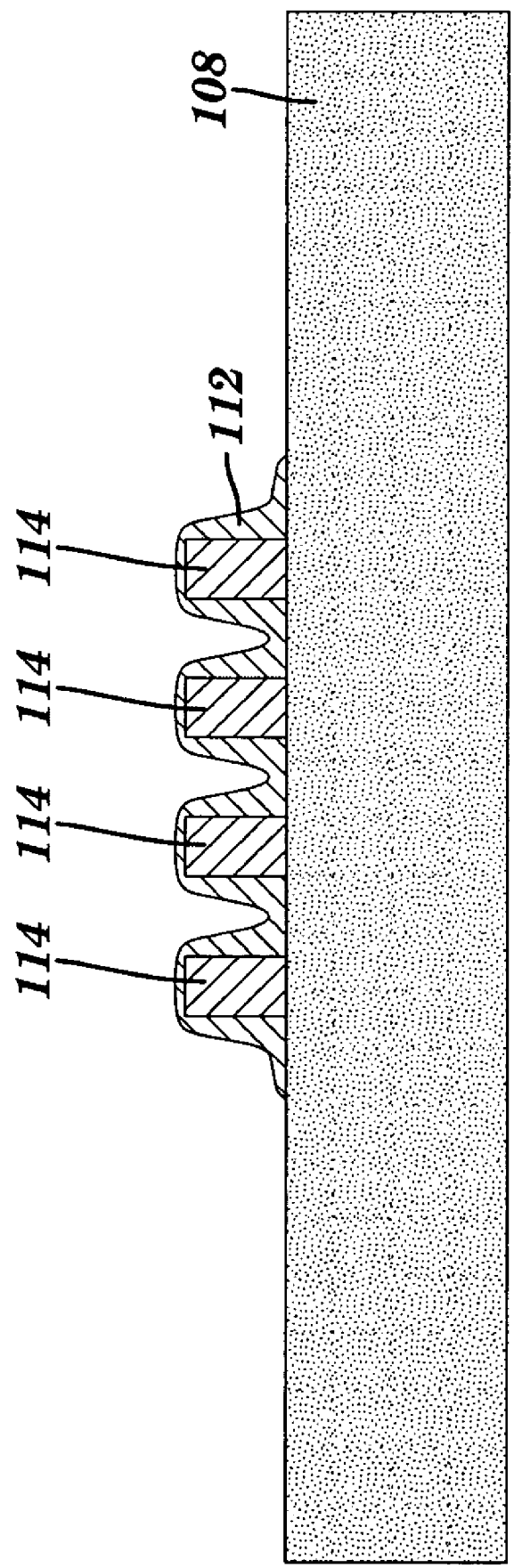
FIG. 4 is a cross sectional view of the localized conductive layer in FIG. 3, particularly illustrating the covering of topographic features on the wafer.

As the precursor gas exits the delivery tube 106 around the target area, the deposition of a conductive layer (e.g., platinum) occurs at areas upon which the electron beam is brought into contact with the surface of the wafer 108. Thus, by precise control of the scan location and pattern of the low-energy electron beam, 110, a local conductive layer deposition may be implemented, characterized by a desired pattern and thickness. As shown in the plan view of FIG. 3 and the cross sectional view of FIG. 4, a localized conductive layer 112 is formed on the surface of the wafer 108, covering various topographic features 114 of interest. In the example depicted, the area of localized conductive layer 112 may be on the order of about 1 micron by 10 microns, and can be formed from materials such as platinum, tungsten, gold, aluminum, titanium, etc. However, platinum is particularly advantageous as it is quite stable and can be formed at thin thicknesses. For example, the electron beam initiated coating of the conductive layer 112 may be formed at an initial thickness from about 10 nanometers (nm) to about 100 nm.

By not implementing a blanket deposition of the conductive layer 112, the present approach avoids unnecessary coverage of wafer real estate located outside the area of interest with respect to the TEM inspection. Moreover, as opposed to an ion beam initiated metal coating, the low-energy electron beam initiated coating avoids edge rounding, topography damage, lack of boundary clarity, and other undesired defects associated with ion beam encapsulation.

Once the initial conductive layer 112 is formed, however, the thickness of this "pre-coated" area may then be enhanced by ion beam coating to increase layer 112 to a desired thickness for throughput purposes, in order to attain a certain thickness which should be thicker than sacrificial thickness milled out during TEM sample preparation. The initial thickness of layer 112, formed by electron beam coating, sufficiently protects the topography of interest 114 on the wafer 108 from deleterious effects of the higher-energy, ion beam deposition process.

Figure 5:
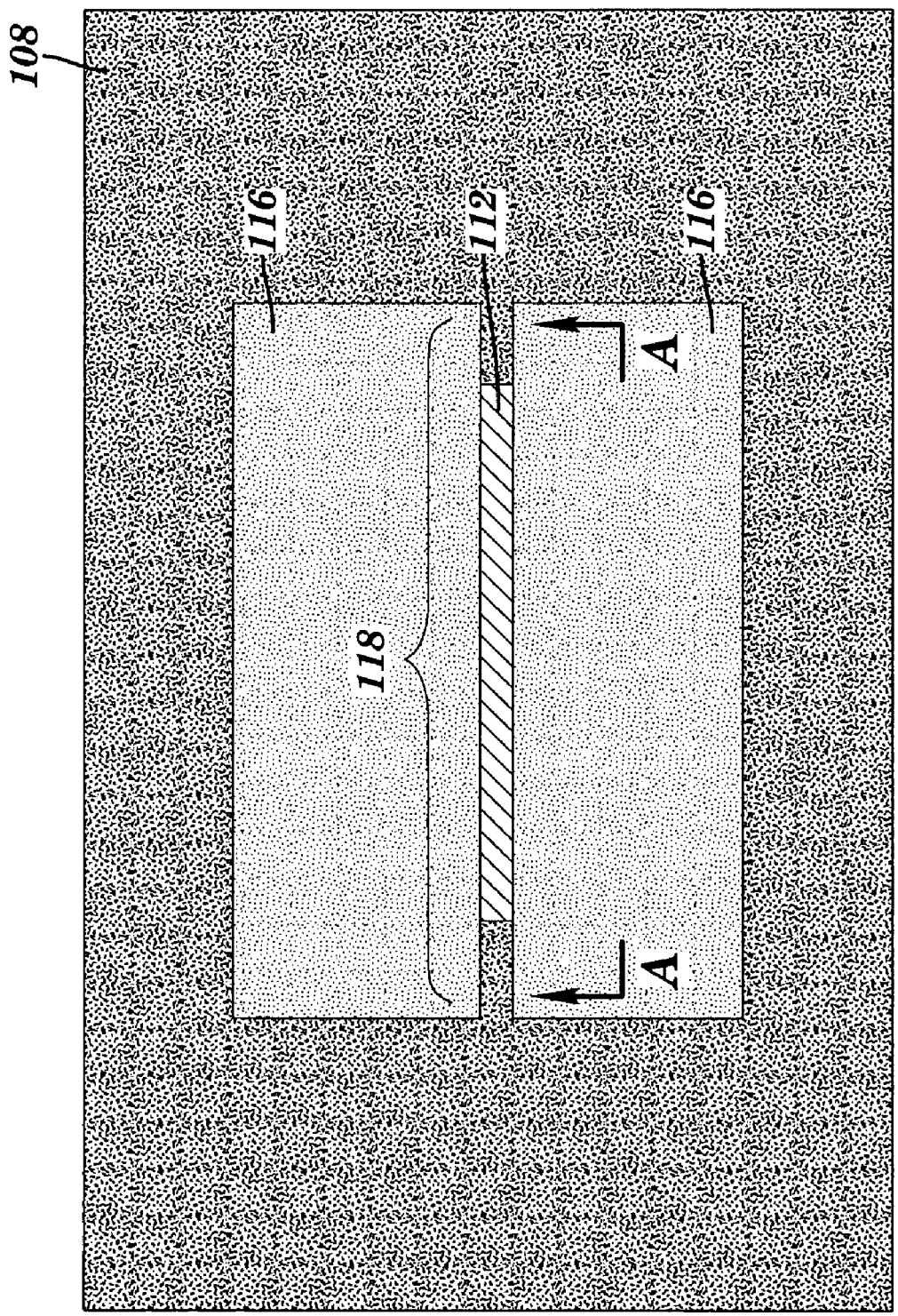
FIG. 5 is plan view of the metal coated wafer of FIG. 3, following the optionally enhanced thickness of the initial conductive layer and following the formation of ion-milled trenches used to excise the sample for TEM inspection.

As shown in FIG. 5, the focused ion beam column 102 (FIG. 1) is then used to mill out a pair of adjacent trenches 116 within the bulk material of the wafer 108. Thus formed, the trenches 116 are disposed with respect to one another so as to form a membrane 118 of wafer substrate and metal-encapsulated material, having an exemplary thickness of about 100 nm. The trenches 116 are further milled to a depth sufficient to allow the membrane 118 to be physically removed from the rest of the wafer 108 through a micro-manipulator or other suitable excision tool known in the art.

Figure 6:
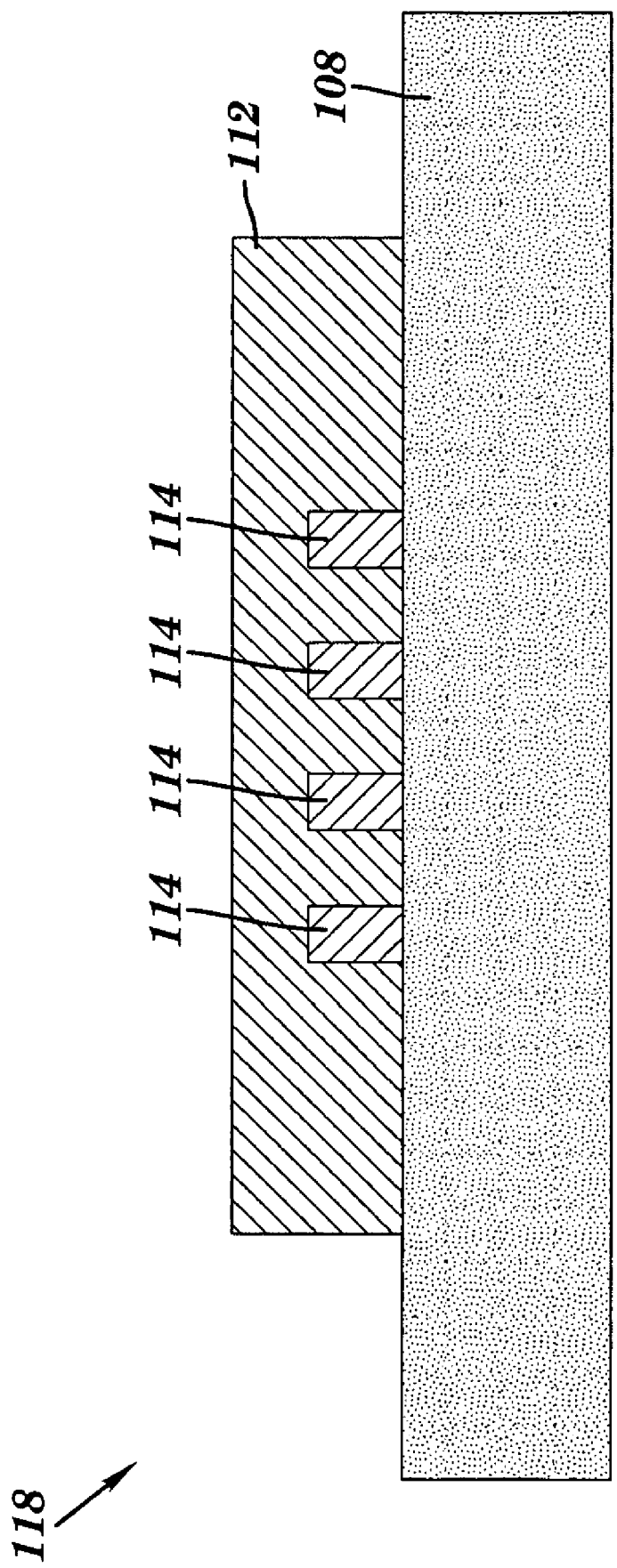
FIG. 6 is a cross sectional view of the removed TEM sample, taken along arrows A—A of FIG. 5, illustrating the protective metal coating formed by low-energy electron beam deposition.

Finally, FIG. 6 is cross-sectional view of the removed membrane 118 (taken along arrows A—A of FIG. 5 that is used as a sample for TEM inspection. As is shown, the metal layer 112 protects the various topographic features 114 of interest formed on the substrate surface of the removed wafer section 108. Because the metal coating layer 112 (e.g., platinum) is formed through electron beam deposition, the original profile of the topographic features 114 is better preserved. Moreover, the preserved topography may be used for the original feature metrology such as, for example, the critical dimension (CD) measurement for line, space, contact hole, pillar, and other shapes widely used in semiconductor industry.

While the invention has been described with reference to a preferred embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for preparing a specimen for application of microanalysis thereto, the method comprising:
    forming an initial conductive layer over only a localized area of interest, said initial conductive layer formed through a low-energy beam deposition process;
    removing a volume of material surrounding said area of interest by forming a pair of trenches in a bulk material having said area of interest formed thereon, thereby forming a membrane including said area of interest and said initial conductive layer over said area of interest; and
    removing said membrane from said bulk material.

2. The method of claim 1, wherein said low-energy beam deposition process comprises electron beam deposition.

3. The method of claim 2, wherein said initial conductive layer further comprises at least one of: platinum, tungsten, gold, aluminum, titanium, and combinations thereof.

4. The method of claim 1, wherein said initial conductive layer is formed at a thickness of about 10 nanometers (nm) to about 100 nm.

5. The method of claim 4, wherein said initial conductive layer is formed over an area of about 1 micron by about 10 microns.

6. The method of claim 4, further comprising implementing a high-energy beam deposition process for increasing the thickness of said initial conductive layer.

7. The method of claim 6, wherein said high-energy beam deposition process comprises ion beam deposition.

8. The method of claim 1, wherein said removing a volume of material surrounding said area of interest is implemented by focused ion beam milling.

9. A method for preparing a specimen for application of microanalysis thereto, the method comprising:
    forming an initial conductive layer over a defined, localized area of interest on a substrate, without blanket coverage of said initial conductive layer on the entire substrate, said initial conductive layer formed through an electron beam deposition process;
    removing a volume of substrate material surrounding said area of interest, thereby forming the specimen, including said area of interest and said initial conductive layer over said area of interest; and
    removing the specimen from said substrate material.

10. The method of claim 9, wherein the microanalysis comprises tunneling electron microscopy (TEM).

11. The method of claim 10, wherein said initial conductive layer further comprises at least one of: platinum, tungsten, gold, aluminum, titanium, and combinations thereof.

12. The method of claim 9, wherein said initial conductive layer is formed at a thickness of about 10 nanometers (nm) to about 100 nm.

13. The method of claim 12, wherein said initial conductive layer is formed over an area of about 1 micron by about 10 microns.

14. The method of claim 12, further comprising implementing a high-energy beam deposition process for increasing the thickness of said initial conductive layer.

15. The method of claim 14, wherein said high-energy beam deposition process comprises ion beam deposition.

16. The method of claim 9, wherein said removing a volume of substrate material surrounding said area of interest is implemented by focused ion beam milling.

* * * * *